(12) United States Patent
Andersson

(10) Patent No.: US 9,555,120 B2
(45) Date of Patent: Jan. 31, 2017

(54) CHITOSAN COMPOSITION

(75) Inventor: Mats Andersson, Stockholm (SE)

(73) Assignee: VISCOGEL AB, Stockholm (SE)

( * ) Notice: Subject to any disclaimer, the term of this patent is extended or adjusted under 35 U.S.C. 154(b) by 751 days.

(21) Appl. No.: 13/696,023

(22) PCT Filed: Apr. 15, 2011

(86) PCT No.: PCT/EP2011/056064
§ 371 (c)(1),
(2), (4) Date: Mar. 28, 2013

(87) PCT Pub. No.: WO2011/138155
PCT Pub. Date: Nov. 10, 2011

(65) Prior Publication Data
US 2013/0184356 A1    Jul. 18, 2013

Related U.S. Application Data

(60) Provisional application No. 61/331,053, filed on May 4, 2010.

(51) Int. Cl.
| | |
|---|---|
| *A61K 47/36* | (2006.01) |
| *C09K 15/20* | (2006.01) |
| *A61K 9/00* | (2006.01) |
| *A61K 9/06* | (2006.01) |
| *A61K 9/107* | (2006.01) |
| *A61K 9/16* | (2006.01) |
| *A61K 9/50* | (2006.01) |
| *A61K 31/337* | (2006.01) |
| *A61K 31/4439* | (2006.01) |
| *A61K 31/58* | (2006.01) |
| *A61K 31/593* | (2006.01) |
| *C08B 37/08* | (2006.01) |
| *C08L 5/08* | (2006.01) |
| *C08J 3/075* | (2006.01) |
| *A61K 39/00* | (2006.01) |

(52) U.S. Cl.
CPC ............ *A61K 47/36* (2013.01); *A61K 9/0019* (2013.01); *A61K 9/06* (2013.01); *A61K 9/107* (2013.01); *A61K 9/1652* (2013.01); *A61K 9/1682* (2013.01); *A61K 9/5036* (2013.01); *A61K 9/5089* (2013.01); *A61K 31/337* (2013.01); *A61K 31/4439* (2013.01); *A61K 31/58* (2013.01); *A61K 31/593* (2013.01); *C08B 37/003* (2013.01); *C08J 3/075* (2013.01); *C08L 5/08* (2013.01); *C09K 15/20* (2013.01); *A61K 39/00* (2013.01); *C08J 2305/08* (2013.01)

(58) Field of Classification Search
None
See application file for complete search history.

(56) References Cited

U.S. PATENT DOCUMENTS

2007/0248675 A1 * 10/2007 Tae et al. .................. 424/486
2010/0291055 A1 * 11/2010 Athanasiadis et al. ...... 424/94.1

FOREIGN PATENT DOCUMENTS

| CA | 1329121 C | 5/1994 |
|---|---|---|
| JP | 64-3116 A | 1/1989 |
| JP | 9-67273 A | 3/1997 |
| RU | 2093145 C1 | 10/1997 |
| WO | 2009/056602 A1 | 5/2009 |

OTHER PUBLICATIONS

International Search report issued in PCT/EP2011/056064 dated Aug. 12, 2011.
Obara et al., "Controlled Release of Paclitaxel from Photocrosslinked Chitosan Hydrogels and its Subsequent Effect on Subcutaneous Tumor Growth in Mice". Journal of Controlled Release, vol. 110, No. 1 pp. 79-89 (Dec. 10, 2005).
Ganguly Sudipta et al., "A Novel in situ Gel for Sustained Drug Delivery and Targeting". International Journal of Pharmaceutics, vol. 276, No. 1-2, pp. 83-92 (May 19, 2004).
Jauhari Saurabh et al., "A Mucoadhesive in situ Gel Delivery System for Paclitaxel", AAPS Pharmscitech, vol. 7, No. 2, E53, pp. E1-E6, (2006).
English translation of Japanese Office Action dated Mar. 3, 2015 issued in Japanese Patent Application No. 2013-508422.
English translation of Russian Federation Office Action dated Aug. 25, 2015 issued in Russian Patent Application No. 2012148780/15(078361).

* cited by examiner

*Primary Examiner* — Robert A Wax
*Assistant Examiner* — Randeep Singh
(74) *Attorney, Agent, or Firm* — McDermott Will & Emery LLP

(57) ABSTRACT

This invention provides a composition comprising: (i) a chitosan hydrogel comprising cross-linked chitosan and water; and (ii) a liquid dispersed in the hydrogel.

19 Claims, 3 Drawing Sheets

CHITOSAN COMPOSITION

RELATED APPLICATIONS

This application is the U.S. National Phase under 35 U.S.C. §371 of International Application No. PCT/EP2011/056064 filed on Apr. 15, 2011, which in turn claims priority from U.S. 61/331,053 dated May 4, 2010. the disclosures of which Applications are incorporated by reference herein.

This invention relates to a chitosan composition, and particularly to a cross-linked chitosan hydrogel comprising a dispersed liquid.

Colloidal systems in which one substance is dispersed evenly through another find numerous technical applications. Dispersions and emulsions are examples of colloidal systems. A dispersion is defined as a system in which particles are dispersed in a continuous phase of a different composition or state. An emulsion is a colloidal system in which both the dispersed phase and the continuous phase are liquids. Oil-in-water emulsions (O/W) contain oil droplets dispersed in an aqueous continuous phase, whereas water-in-oil emulsions (W/O) contain liquid droplets dispersed in a continuous phase that is an organic liquid. More complex systems such as oil droplets contained within aqueous droplets dispersed in a continuous oil phase (O/W/O) are also known.

Emulsions are thermodynamically unstable, which means that stabilisation is required to prevent aggregation or coalescence of the dispersed phase. Emulsifiers are therefore used to enhance the colloidal stability of emulsions. Emulsifiers are surface active materials that adsorb at the interface between the dispersed phase and the continuous phase, lowering the interfacial tension. Emulsifiers stabilise the emulsion by decreasing the rate of aggregation and/or coalescence of the dispersed phase. Many different types of emulsifiers are known but existing emulsifiers have a number of disadvantages. For example, commonly used emulsifiers are known to have low biodegradability which means that they accumulate on release into the environment, potentially causing pollution. In particular, some emulsifiers are known to be toxic to marine life.

Owing to the thermodynamic instability of emulsions, separation of the liquid phases can occur when emulsions are stored for prolonged periods. Furthermore, many emulsions are sensitive to environmental stresses such as shear forces and changes in temperature. This means that the packaging, storage and transport of emulsions for commercial use can be problematic. Despite these disadvantages, emulsions find use in many industries, such as the pharmaceutical, cosmetic, food, agrochemical, oil, engineering, textile, paper and home and personal care product industries. In many of these industries there is an on-going need for more stable emulsions.

In the pharmaceutical sector, water-insoluble drugs provide formulation scientists with significant challenges. In order to improve the solubility in vivo, and therefore improve the bioavailability of the drug, water-insoluble drugs are often provided in aqueous media together with surfactants or nanoparticle-based delivery agents. The anti-cancer drug paclitaxel, for example, is currently provided as a concentrate solution in Cremophor EL (macrogolglycerol ricinoleate) and ethanol. In this particular delivery system water is initially avoided since paclitaxel is sensitive to water in which it slowly hydrolyses. The solution is then diluted with an aqueous physiological solution, for example Ringer's solution before infusion. The use of Cremophor EL has been associated with side effects such as severe anaphylactoid hypersensitivity reactions.

There remains therefore a need in the art for compositions which overcome the above-described disadvantages.

Accordingly, the present invention provides a composition comprising: (i) a chitosan hydrogel comprising cross-linked chitosan; and (ii) a liquid dispersed in the hydrogel.

The present invention also provides a process for preparing the composition of the invention, the process comprising: providing a cross-linkable chitosan composition comprising chitosan and water; dispersing a liquid in the cross-linkable chitosan composition; and cross-linking the chitosan with a cross-linking agent to form a hydrogel.

Thus, the present invention provides chitosan hydrogels which can be used to provide more stable colloidal systems.

The present invention will now be described with reference to the accompanying drawings, in which.

Figure 1:
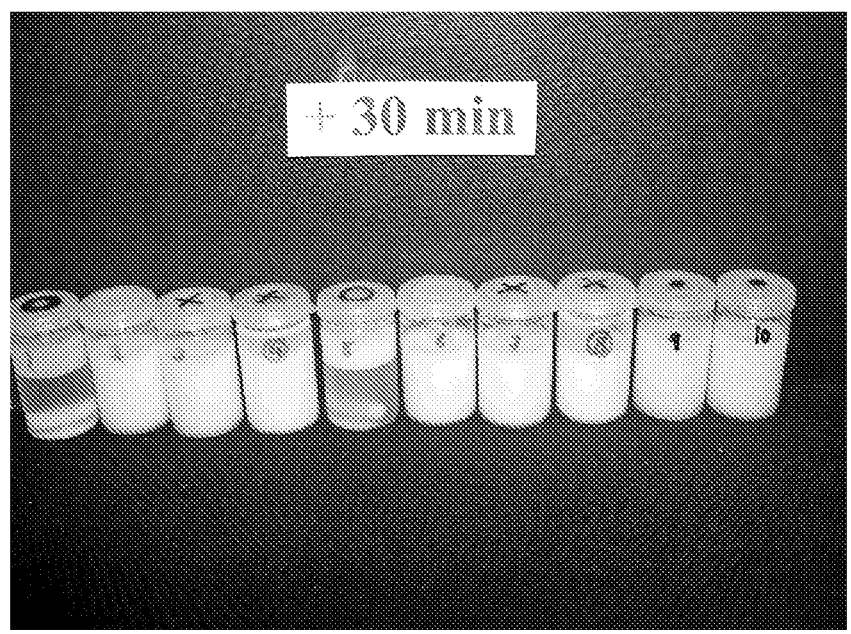
FIG. 1 shows a photograph of emulsions of the present invention and comparative emulsions after standing for 30 mins.

The composition of the present invention comprises a liquid dispersed in the hydrogel. This means that water-immiscible liquid droplets are distributed in a finely divided state throughout the hydrogel. The compositions of the invention are therefore analogous to an emulsion where the liquid droplets are dispersed in a chitosan hydrogel continuous phase. By hydrogel is meant a colloidal gel in which water is the dispersion medium.

The improved stability of the compositions of the invention allows the compositions to be stored for long periods. Furthermore, it is believed that lower concentrations of emulsifier can be used to produce a stable emulsion. Although not wishing to be bound by theory, it is thought that the cross-linked chitosan provided in the hydrogel produces a cage-type structure around the dispersed liquid droplets which helps to prevent aggregation or coalescence of the dispersed material.

Chitosan is a linear polysaccharide composed of 1,4-beta-linked D-glucosamine and N-acetyl-D-glucosamine residues. Chitosan is produced by alkaline deacetylation of chitin, which is a polymer of a N-acetyl-D-glucosamine found in shells of crustaceans. Chitosan of high molecular weight and/or high degree of N-deacetylation is practically insoluble in water; however its salts with monobasic acids tend to be water-soluble. The average pKa of the glucosamine residues is about 6.8 and the polymer forms water-soluble salts with e.g. HCl, acetic acid, and glycolic acid.

Chitosan is biodegradable, non-toxic and anti-microbial. Furthermore, its cationic and hydrophilic nature makes it attractive in pharmaceutical formulations.

Chitosan is characterised by its molecular weight and degree of deacetylation. Chitosans of different molecular weights and degrees of deacetylation can be produced by varying the conditions of the chitin alkali treatment. Commercially, chitosans are characterised by their viscosity and an average molecular weight is given. Commercially available chitosans typically have molecular weights in the range of 4 to 2,000 kDa and average degrees of deacetylation of 66 to 95%.

Chitosan is polydisperse in its nature, i.e. contains a mixture of different chain lengths. Chitosan used according to the present invention preferably has a viscosity of up to 15,000 mPas prior to cross-linking, preferably from 2 to 10,000 mPas, more preferably from 5 to 2,000 mPas and most preferably from 10 to 1,000 mPas when measured as a 1% w/v solution in 1% aqueous acetic acid at a temperature of 25° C. using a rotating viscometer with a spindle rotating at 20 rpm. The viscosity of the solution is an indication of the average molecular weight of the chitosan, it being understood that chitosan is a polymeric material having a distribution of molecules of varying chain length. The chitosan preferably has a weight average molecular weight of 10 to 500 kDa. Weight average molecular weights can be determined using light scattering techniques.

The pattern of the deacetylation of the chitosan is also important for its properties. Commercially available chitosan typically has a block structure, which means that the chitosan includes blocks of N-acetyl-D-glucosamine residues, or blocks of chitin-like polymer. This is because chitin is typically isolated in solid phase processes from crustacean shells. In such processes, in which the shells remain undissolved throughout the process, the shells are treated with strong alkali to give the partially deacetylated chitosan. However, because the chitin is initially in the form of crustacean shell, the hydroxide ions of the alkali tend to act preferentially on the monosaccharide units on the surface of the shell; the monosaccharide units within the centre of the relatively thick shell tend not to see the hydroxide ions and hence retain the N-acetyl substitution pattern.

The solubility of chitosan depends on chitosan chain length, degree of deacetylation, acetyl group distribution within the chains, and external conditions such as ionic strength, pH, temperature, and solvent. Practically, most commercially available, unmodified chitosans have a degree of deacetylation exceeding 80% and are insoluble in aqueous solution when the pH is above approximately 6: above this pH they will precipitate from aqueous solution.

When a hydrogel is the desired product it is essential that the chitosan and the cross-linked derivative remain in solution and that precipitation thereof is avoided.

The chitosan hydrogels for use in the present invention can be made using known methods for cross-linking chitosan. In these methods, the chitosan hydrogels are produced by solubilising chitosan in aqueous solution and cross-linking the chitosan. Thus, commercially available chitosan is cross-linked in aqueous solution at a pH at which the chitosan is soluble, typically in acidic solution, for example pH 4-5. These hydrogels are stable at low pH (pH 5 or less) and are therefore useful in the compositions of the invention when a low pH is required for any particular end use.

Preferably the chitosan hydrogel of the present invention is produced from chitosan that has a degree of deacetylation 75% or less, more preferably 70% or less, more preferably 65% or less, more preferably 60% or less and most preferably 55% or less. Chitin is completely insoluble in water and becomes soluble to some extent when the degree of deacetylation is 30% or more. The chitosan according to the present invention therefore preferably has a degree of deacetylation above 35%, preferred is a degree of deacetylation above 40% and most preferred is a degree of deacetylation above 45%.

Although the chitosan used to produce the hydrogel of the present invention can have a block pattern of deacetylation, preferably the chitosan used to produce the hydrogel of the present invention is randomly deacetylated. That is, the chitosan has a random pattern of acetylated and deacetylated monosaccharide units. One way of determining the nature of the monosaccharides is to determine the nearest-neighbour frequencies using NMR and compare the frequencies obtained with statistical models, see WO 03/011912.

Chitosan having a random deacetylation pattern can be produced by treating chitin in solution under carefully controlled conditions, or by fully deacetylating the chitin and then reacetylating in solution to provide the required degree of deacetylation. See T. Sannan et al Makromol. Chem. 177, 3589-3600, 1976; X. F. Guo at al, Journal of Carbohydrate Chemistry 2002, 21, 149-61; and K. M. Vårum et al Carbohydrate Polymers 25, 1994, 65-70. The chitosan of the present invention is preferably obtainable by acetylating and/or deacetylating the chitosan in the solution phase to provide a random deacetylation pattern.

Preferably the chitosan used to produce the hydrogel of the present invention has a degree of deacetylation of 75% or less and has a random deacetylation pattern.

Chitosan having a degree of deacetylation below 75% and having a random pattern of deacetylation has higher solubility in water compared to typical commercially available chitosans. The low deacetylated/random chitosans are soluble at higher pH, which means that the cross-linking reaction to produce a hydrogel can take place at higher pH. The advantages of doing this are several. The possibility to use a higher pH is beneficial in terms of substantially increased reactivity of the amino groups on the glucosamine residues. This makes the couplings more efficient and enables the use of much lower concentrations of cross-linking reagents to reach a defined degree of cross-linking, leading to low manufacturing costs. Another benefit is that the side reactions are kept low. Another beneficial and important aspect of using low concentrations of cross-linking agent is that when the formed hydrogels are intended for medicinal use, toxic side effects resulting from interactions of the cross-linker and its biological environment could be minimised.

Although the cross-linking of chitosan having a degree of deacetylation below 75% and having a random pattern of deacetylation can be carried out at acidic pH, for example pH 4 to 5, the cross-linking is preferably performed at pH 6 or above. Even more preferred is to use pH above 6.3. It is also preferred to use a pH that does not to a substantial degree destroy the cross-linking reagent by hydrolysis or via an elimination reaction. Typical conditions for the reaction are alkaline conditions, preferably using a pH below 10, more preferably below 9.5 and most preferably below 9.0. The gels produced according to this preferred embodiment of the invention are particularly preferred because they have low toxicity and they can be made to degrade rapidly. As mentioned above, the gels do not precipitate when subjected to neutral and alkaline conditions. They also possess a rigidity which allows for further mechanical processing into e.g. injectable so called "crushed gels", useful in a vast number of applications.

Cross-linking agents suitable for use in the present invention comprise at least two reactive sites which are electrophiles designed to react easily with amines. When the cross-linker has two reactive sites it is bifunctional and can thus react with two amino groups e.g. two glucosamine units in different chitosan chains. The distance between the reactive groups may be increased by a spacer moiety. This spacer is often an aliphatic chain or a polyether construct like poly- or oligoethylene glycols. Preferably the cross-linking agent is bi-, tri- or tetrafunctional, although bi- or trifunctional is preferred and bifunctional is most preferred. It is preferred to use bi-functional cross-linkers that easily react at a pH close to or above the pKa (approximately 6.8) of the glucosamines in the polymer chains in high yielding reactions and in which the cross-linking molecule is consumed to a considerable degree. It is also preferred that the cross-linking molecule does not form by-products that have to be removed prior to use. Many cross-linkers are designed to eliminate a leaving group when reacting. In such cases cross-linkers that eliminate non-toxic components are preferred. Typical examples of such cross-linking functionalities are reactive esters, Michael acceptors and epoxides. Suitable cross-linking agents are known and include glycosaminoglycans such as hyaluronic acid and chondroitin sulfate (Ann. Pharm. Fr. 58 47-53, 2000), glutaraldehyde (Ind. Eng. Chem. Res. 36: 3631-3638, 1997), glyoxal (U.S. Pat. No. 5,489,401), diethyl squarate (Macromolecules 31:1695-1601, 1998), diepoxides such as diglycidyl ether (U.S. Pat. No. 5,770,712), tripolyphosphate (J Appl Polym Sci 74: 1093-1107, 1999), genipin (J Polym Sci A: Polym Chem 38, 2804-2814, 2000, Biomaterials. 23, 181-191, 2002), formaldehyde (J. Polym. Sci. Part A: Polym. Chem. 38, 474, 2000, Bull. Mater. Sci., 29, 233-238, 2006). Preferred cross-linking molecules are ester derivatives of squaric acid, diepoxides and derivatives of acrylamides. Most preferred is diethyl squarate (3,4-diethoxy-3-cyclobutene-1,2-dione) and its structurally closely related analogues. Other preferred cross-linkers are 1,4-butandiol diglycidylether, derivatives of acrylamide and their structurally closely related analogues.

The structure of the hydrogel of the invention is affected by the concentration of chitosan and the amount of cross-linking reagent used. Thus, hydrogels having a higher viscosity can be produced by using a higher concentration of chitosan in the hydrogel, or by increasing the number of cross-links. In general, it is preferred to have higher chitosan concentrations and lower concentrations of cross-linking agent to achieve a gel of the desired nature. It is preferable to minimise the amount of cross-linker used, particularly for pharmaceutical applications, because cross-linkers may cause an immunological response or toxic side reactions if not fully consumed.

The molar ratio of cross-linking agent to chitosan based on the number of functional groups in the cross-linking agent and the number of accessible amino groups in the chitosan is preferably 0.2:1 or less, more preferably 0.16:1 or less and most preferably 0.1:1 or less. The molar ratio is based on the number of groups available for cross-linking on the cross-linker and on the chitosan. For the cross-linker it will depend on the functionality (bi-, tri-, tetrafunctional etc) and on the chitosan to the accessibility of the amino groups (only the deacetylated amino groups will be reactive). Clearly, the number of available amino groups will be determined by the degree of deacetylation of the chitosan.

By way of contrast to the cross-linked hydrogels of the present invention, oil-in-water emulsions based on non-cross-linked chitosan have been proposed (see Mun et al, Journal of Colloid and Interface Science, 2006, 296, 581-590; Laplante et al, Carbohydrate Polymers, 2005, 59, 425-434; Laplante et al, Food Hydrocolloids, 2005, 19, 721-729; and Helgason et al, Journal of Aquatic Food Product Technology, 2008, 17, 3, 216-233). However, these documents disclose a different approach. These documents suggest that in order to provide effective stabilisation, the chitosan should adsorb at the surface of surfactant-stabilised droplets in order to form a multilayer emulsion. However, the large variability in chitosan characteristics such as molecular weight and degree of deacetylation make it difficult to achieve effective stabilisation in this manner. Moreover, it has been found that the compositions of the present invention, which comprise a liquid dispersed in a cross-linked chitosan hydrogel, have improved stability when compared to compositions comprising non-cross-linked chitosan.

The chitosan is preferably present in the composition of the present invention in an amount of 3% by weight or less based on the total weight of chitosan and water in the hydrogel. More preferred is to use an amount of 2% by weight or less. Preferably the amount of chitosan is above 0.3% by weight based on the total weight of chitosan and water in the hydrogel, preferably 0.75% by weight or greater. Water can be present in the hydrogel in amount of up to 99.7% by weight, based on the total weight of the chitosan and water in the hydrogel. However, in many applications a combination of water and one or more other solvents may be used depending on the nature of the intended use of the emulsion systems formed. Examples of such solvents are water-miscible solvents, such as alcohols (e.g. ethanol, glycerol, ethylene glycol or propylene glycol), polyethylene or polypropylene glycols, DMSO, acetone, DMF, glycofuran, methyl pyrrolidone, Transcutol and combinations thereof.

The compositions of the invention can optionally include materials that are miscible or soluble in the hydrogel matrix such as preservatives, inorganic salts such as sodium chloride, and buffers.

The compositions of the invention comprise a liquid dispersed in the hydrogel. In a preferred embodiment, the composition of the invention comprises a water-soluble active agent that is solubilised in the hydrogel. Suitable active agents include water-soluble drugs, vitamins and cosmetic ingredients. The amount of active agent present will very depending on the type of active ingredient and the end use but the active ingredient may be present in an amount of 0.005 to 15% by weight, for example, based on the total weight of the composition.

Suitable liquids are immiscible with water and include any liquid that is able to form the dispersed phase in an oil-in-water emulsion. Examples of suitable liquids are well known and include water-immiscible oils, pharmaceutical active agents and excipients, cosmetic ingredients, vitamins, foods, agrochemical active agents and additives, and personal care ingredients.

It has been found that the compositions of the present invention can comprise up to 50% by weight of dispersed liquid, based on the total weight of the composition and still remain stable. The use of cross-linked chitosan significantly increases emulsion stability. This increase in stability allows high proportions of dispersed liquid to be used. The dispersed liquid is preferably present in an amount of 5 to 30% by weight based on the total weight of the composition.

The dispersed liquid may include a mixture of materials provided that the mixture is dispersible in water. For example, the dispersed liquid may comprise a mixture of two or more liquids that are immiscible with water, or a mixture of a water-immiscible liquid and solid particles dispersed in the water-immiscible liquid.

In one preferred embodiment of the present invention, one or more water-insoluble active ingredients are solubilised in the dispersed liquid. According to this embodiment of the invention, a water-insoluble drug or vitamin, for example, is solubilised in a water-immiscible liquid that is dispersed in the hydrogel. Many examples of water-insoluble active ingredients are known to the person skilled in the art and include insect repellents; dyes; drugs, for example cytostatic drugs such as paclitaxel, anti-inflammatory agents such as budesonide and immunosuppressant drugs such as cyclosporin; and vitamins such as vitamin D and vitamin A.

When the composition includes a drug, for example, the dispersed liquid should be a pharmaceutically acceptable liquid carrier that is immiscible with water. Examples include lipids, e.g. phospholipids, triacyl glycerols, di- and mono alkyl esters of glycerol, and fatty acids, including omega-3 fatty acids such as eicosapentaenoic acid (EPA) and docosahexaenoic acid (DHA). Typically such oils and lipids are sesame oil, sunflower oil, olive oil, rape seed oil, Miglyol® 812 (caprylic/capric triglyceride), paraffin oil and lanolin.

When the compositions of the invention comprise a dispersed liquid, an emulsifier is provided in order to stabilise the liquid droplets. Any emulsifier that is suitable for producing an oil-in-water emulsion can be used. The emulsifier may be anionic, cationic or non-ionic, or a combination thereof. Suitable emulsifiers are well known to the person skilled in the art and include alkyl sulfonates, alkyl sulfosuccinates, phospholipids such as lecithins, proteins, polyethylene glycol-hydrogenated castor oils, copolymers of ethylene oxide and propylene oxide (such as those available under the trade name Pluronic®), polyethylene oxide esters of fatty acids (such as those available under the trade name Myrj®), polyethylene oxide alkyl ethers of fatty alcohols (such as those available under the trade name Brig®), sorbitan fatty acid esters (such as those available under the trade name Span®), alkylphenol ethoxylates (such as those available under the trade name Triton®) and polyethylene oxide sorbitan fatty acid esters (such as those available under the trade name Tween®). In a preferred embodiment, the composition of the present invention further comprises a phospholipid. The phospholipid may advantageously form a liposomal phase which is stabilised by the chitosan hydrogel.

The emulsifier is present in an amount that is suitable for stabilising an oil-in-water emulsion and can be easily determined by the person skilled in the art. It has been surprisingly found that the compositions of the present invention can include relatively low amounts of emulsifier and still give emulsions of higher stability than the corresponding non-cross-linked emulsion. Although not wishing to be bound by theory, it is believed that the use of cross-linked chitosan significantly increases emulsion stability, allowing lower concentrations of emulsifier to be used. The emulsifier can therefore be present in the compositions of the invention in an amount of 0.2 to 25% by weight, more preferably 0.2 to 5.0% by weight, based on the weight of the dispersed liquid.

In preferred embodiments of the invention it has been found that the amount of emulsifier could be substantially reduced providing compositions of superior stability to the corresponding emulsions comprising non-cross-linked chitosan in which the concentration of the emulsifier was a five fold higher. In addition, stable compositions of very high lipid content, 50%, may be made, including under conditions normally considered more demanding, such as in a physiological salt concentration.

As discussed hereinabove, the compositions are produced by providing a cross-linkable chitosan composition comprising chitosan and water; dispersing a liquid in the cross-linkable chitosan composition; and cross-linking the chitosan with a cross-linking agent to form a hydrogel. It is believed that the cross-linked chitosan provided in the hydrogel produces a cage-type structure around the dispersed liquid droplets, which helps to prevent aggregation or coalescence of the dispersed material. In the process for producing the hydrogel at least some of the cross-linking should therefore take place after the liquid has been dispersed in the cross-linkable chitosan composition.

The liquid to be dispersed is added to the cross-linkable chitosan composition and the mixture is stirred. High-speed mixers suitable for use in preparing emulsions and colloidal suspensions can be used and these are well known. Homogenisation under high pressure is also commonly used for this purpose.

The cross-linking agent can be added to the cross-linkable chitosan composition before, at the same time or after the liquid to be dispersed. Preferably the cross-linking agent is added to the cross-linkable chitosan composition before the liquid is dispersed in the chitosan composition. This means that the cross-linking reaction commences before the liquid is dispersed in the composition. However, the liquid should be dispersed in the chitosan composition before the cross-linking reaction is complete. According to this preferred embodiment, liquids can easily be dispersed in the cross-linkable chitosan composition simply by stirring with a magnetic stirrer at room temperature: a high speed mixer is not required.

The cross-linkable chitosan must remain solubilised in the aqueous medium while the cross-linking reaction takes place. A discussed hereinabove, the pH can be adjusted to ensure that the chitosan remains soluble. Thus, for many commercially available chitosans, the cross-linking reaction will take place at acidic pH, typically pH 4 to 5. However, the low deacetylated chitosans of the preferred embodiment of the invention can be cross-linked at higher pH, typically pH 6 to 10, preferably 6 to 8.

When the composition of the invention comprises materials that are miscible or soluble in the hydrogel matrix such as active agents, preservatives, inorganic salts and buffers, these can be conveniently added to the cross-linkable chitosan composition before the liquid is dispersed in the composition and before cross-linking takes place.

When the composition of the invention comprises one or more water-insoluble active materials dissolved in the dispersed liquid, the water-insoluble materials are solubilised in the liquid before the liquid is dispersed in the cross-linkable chitosan composition.

The hydrogel according to the invention is obtained as a block which may be isolated without further treatment. The hydrogel can be processed to provide smaller blocks or fragments using conventional techniques known in the art. This resulting "crushed gel" could be made with various block/fragment sizes depending on the intended use of the crushed gel. When the blocks are made small they become injectable through a fine needle.

In one embodiment of the invention, substances can be added to the composition after the composition has been processed into a crushed gel.

The viscosity of the gel can be measured with a rheometer such as the Bohlin Gemini VOR instrument, using for measurement cell the cone-plate geometry of 40 mm diameter and a cone angle of 4°, at 25° C.

The present invention will now be described with reference to the following examples, which are not intended to be limiting.

EXAMPLES

Chitosan of low degree of N-deacetylation and having a random deacetylation pattern was prepared essentially following the principles outlined in: Sannan T, Kurita K, Iwakura Y., Studies on Chitin, 1. Die Makromolekulare Chemie 1975, 0, 1191-5; Sannan T, Kurita K, Iwakura Y., Studies on Chitin, 2. Makromol. Chem. 177, 3589-3600, 1976; Guo X, Kikuch, Matahira Y, Sakai K, Ogawa K., Water-soluble chitin of low degree of deacetylation, Journal of Carbohydrate Chemistry 2002, 21, 149-61; and WO 03/011912.

Materials

Chitosan, degree of deacetylation 48%, viscosity 354 mPas (chitosan DD 48%)

Chitosan, degree of deacetylation 63%, viscosity 230 mPas (chitosan DD 63%)

Chitosan, degree of deacetylation 49%, viscosity 69 mPas (chitosan DD 49%)

Chitosan, degree of deacetylation 44%, viscosity 450 mPas (chitosan DD 44%)

PBS—phosphate buffered saline

Rape seed oil, peanut oil, castor oil, Miglyol 812 (caprylic/capric triglyceride)—water-immiscible liquids Polysorbate 60, Tween 20, Brij 52, Triton X-100, Phosal 53 MCT—emulsifiers 3,4-Diethoxy-3-cyclobuten-1,2-dione (diethyl squarate)—cross-linking agent Propylene glycol, PEG 400, ethanol—water-miscible, non-toxic solvents Vitamin D3, esomeprazole sodium, paclitaxel, budesonide—poorly water-soluble active agents Methyl-4-hydroxybenzoate, propyl-4-hydroxybenzoate—water-soluble active agent A. Comparison of Emulsions Formed in PBS, Chitosan and Cross-Linked Chitosan.

Preparation of Chitosan Solution 1.25% w/v (100 mL)

Chitosan DD 48% (1.25 g) was added to a beaker equipped with a stir bar. Water (approximately 80 mL) was added and pH adjusted by dropwise addition of hydrochloric acid ($2M_{(aq)}$) under constant stirring. When the chitosan had dissolved the pH was adjusted to 6.6 and the volume was adjusted to 100 mL.

Preparation of Chitosan Solution 0.625% w/v (100 mL)

To the chitosan solution above (50 mL) was added an identical volume of water and the solution was thoroughly mixed.

Preparation of Rape Seed Oil-Polysorbate Stock Solutions

Stock Solution A:

Polysorbate 60 (2 g) was stirred at room temperature in rape seed oil (25 g) until a homogeneous and slightly opaque solution had formed.

Stock Solution B:

Polysorbate 60 (380 mg) was stirred at room temperature in rape seed oil (25 g) until a transparent solution had formed Preparation of Diethyl Squarate Stock Solution in Ethanol (3,4-diethoxy-3-cyclobuten-1,2-dione) (50 μL) was dissolved in ethanol (950 μL).

Activation of chitosan solution with 3,4-diethoxy-3-cyclobuten-1,2-dione

To the chitosan stock solution (50 mL), described above, was added diethyl squarate stock solution (315 μL). The solution was stirred at room temperature for at least 15 minutes, to secure efficient mixing, before it was used in the preparation of the emulsions.

Preparation of Emulsions, General Procedure.

The aqueous phase containing PBS, chitosan or chitosan and a cross-linker was vigorously stirred by a magnetic stir bar on a magnetic stirrer. To the aqueous phase was then slowly added rapeseed oil/polysorbate 60 stock solution. A white emulsion was readily formed and the emulsions were stirred for about 1 min. To further secure good mixing, the emulsions were sucked back and forth in a Pasteur pipette (approximately 5 times).

Examples 3, 4, 7, 8 and 10 and Comparative Examples 1, 2, 5, 6 and 9 having the compositions shown in Table 1 were prepared.

TABLE 1

| Example | Stock A (g) | Stock B (g) | Chitosan, 1.25%, non-cross-linked (g) | Chitosan, 0.625%, non-cross-linked (g) | Activated chitosan, 1.25% (g) | Activated chitosan, 0.625% (g) | PBS (g) |
|---|---|---|---|---|---|---|---|
| 1 (comp) | | 2.5 | | | | | 7.5 |
| 2 (comp) | | 2.5 | 7.5 | | | | |
| 3 | | 2.5 | | | 7.5 | | |
| 4 | | 5.0 | | | 5.0 | | |
| 5 (comp) | 2.5 | | | | | | 7.5 |
| 6 (comp) | 2.5 | | 7.5 | | | | |
| 7 | 2.5 | | | | 7.5 | | |
| 8 | 5.0 | | | | 5.0 | | |
| 9 (comp) | | 2.5 | | 7.5 | | | |
| 10 | | 2.5 | | | | 7.5 | |

After mixing the emulsions were stored at 40° C. The chitosan solutions comprising the cross-linker became gradually more rigid and formed a gel overnight. The containers comprising the cross-linked gels could be turned upside down and the gels did not flow. These emulsions could further be mechanically processed to "crushed gels", i.e. small gel blocks that are individually separated and have the consistency of a gel.

Figure 2:
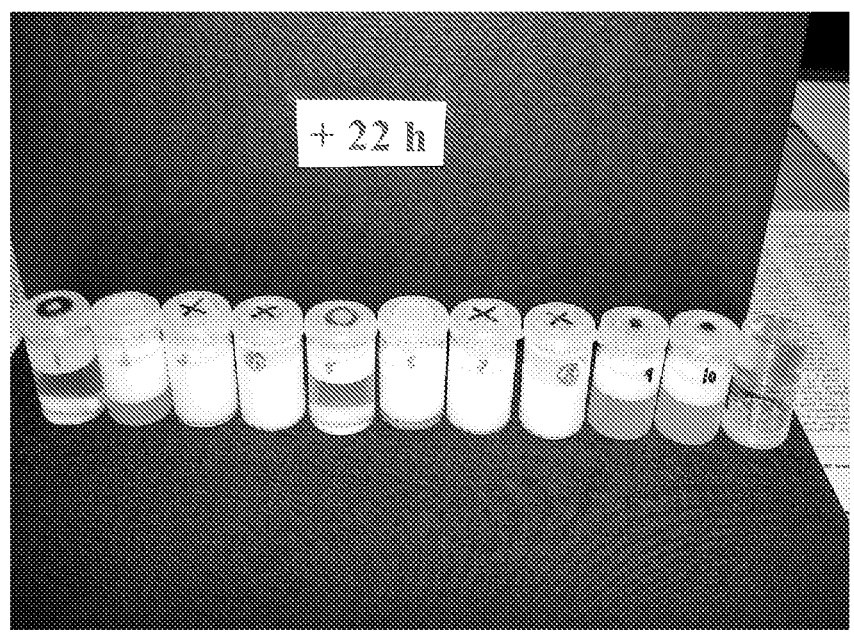
FIG. 2 shows a photograph of the emulsions after standing for 22 hours.
Figure 3:
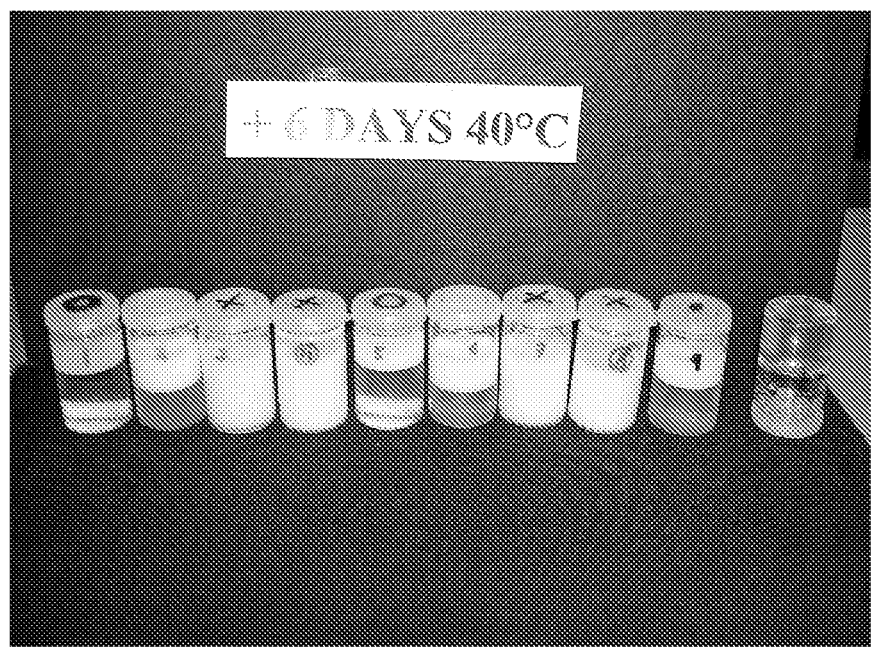
FIG. 3 shows a photograph of the emulsions after standing for 6 days.

The emulsions were stored at 40° C. for 6 days and observed for phase separation. The emulsions formed in PBS (Comparative Examples 1 and 5) were highly unstable and phase separated within a few minutes. The remaining emulsions showed no sign of phase separation after 30 minutes (see FIG. 1). After 22 hours two of the emulsions containing non-cross-linked chitosan (Comparative Examples 2 and 6) were beginning to phase separate and Comparative Example 9, also containing non-cross-linked chitosan, had completely phase separated (see FIG. 2). The emulsion of Example 10, which contained a low concentration of cross-linked chitosan also phase separated after 22 hours. The emulsions of Examples 3, 4, 7 and 8, all of which contained cross-linked chitosan did not phase separate even after storage at 40° C. for 6 days, however (see FIG. 3).

The emulsions of Examples 3, 4, 7 and 8 were further subjected to a freeze-thaw cycle in an attempt to further destabilise the emulsions. The emulsions remained stable after freezing to −18° C. and thawing to room temperature. Example 4 had a very small amount of liquid separated on top of the emulsion phase.

The emulsions of Examples 3 and 4 comprise a low concentration of emulsifier and the emulsions of Examples 4 and 8 comprise a high concentration of dispersed oil. These emulsions may therefore be expected to have decreased stability. As demonstrated above, however, the emulsions of these examples were surprisingly stable upon storage at 40° C. and when subjected to a freeze-thaw cycle.

B. Investigation of Different Emulsifiers and their Impact on Emulsion Formation Preparation of chitosan DD 48% solution 1.25% w/w (100 mL) As described previously.

Preparation of Diethyl Squarate Stock Solution in Ethanol (3,4-diethoxy-3-cyclobuten-1,2-dione) (58.6 mg) was dissolved in ethanol (950 µL).

Activation of chitosan solution with 3,4-diethoxy-3-cyclobuten-1,2-dione

To a chitosan stock solution (80 mL), prepared as described above, was added diethyl squarate stock solution (480 µL). The solution was stirred at room temperature for at least 15 minutes, to secure efficient mixing, before it was used in the preparation of the emulsions.

Preparation of Emulsions

Examples 11 to 15 having the compositions shown in Table 2 were prepared as described above. Oil and emulsifiers were pre-mixed before addition to the aqueous phase

TABLE 2

| Example | Emulsifier | Rape seed oil (g) | Activated chitosan solution (g) | Other ingredients |
|---------|-----------|-------------------|-------------------------------|-------------------|
| 11 | Brij 52 (496 mg) | 2.6 | 7.5 | — |
| 12 | Tween 20 (231 mg) | 2.5 | 7.5 | — |
| 13 | Tween 60 (280 mg) | 2.5 | 7.5 | — |
| 14 | Triton-X-100 (234 mg) | 2.5 | 7.5 | — |

The compositions were stored overnight at 40° C. All samples solidified and formed visually homogeneous and solid "emulsions". The compositions were stored at 40° C. and no phase separation was observed after 9 days.

C. Chitosan Emulsions as Carriers of Drugs and an Emulsion Formed in Saline Conditions Preparation of Chitosan Solution (1.38 w/w) (64 mL)

Chitosan DD 63% (882 mg) was dissolved by dropwise addition of 2M HCl under constant stirring. The pH was adjusted to 6.8 and the volume adjusted to 64 mL.

Preparation of Diethyl Squarate Stock Solution in Ethanol (3,4-diethoxy-3-cyclobuten-1,2-dione) (57 mg) was dissolved in ethanol (950 µL).

Preparation of Rape Seed Oil-Polysorbate Stock Solution

Stock Solution A:

Polysorbate 60 (2 g) was stirred at room temperature in rape seed oil (25 g) until a homogeneously and slightly opaque solution had formed.

Preparation of Emulsions

Examples 15 to 19 having the composition shown in Table 3 were prepared as described above. The hydrophobic drugs/vitamins were dissolved/pre-mixed in their respective hydrophobic phases before they were added to the activated chitosan solution. In Example 19 hereinbelow, NaCl was dissolved in the chitosan-containing phase before addition of the hydrophobic phase.

TABLE 3

| Example | Hydrophobic phase | Drug (mg) | Activated chitosan solution (g) | Activated chitosan + NaCl solution (g) |
|---------|-------------------|-----------|---------------------------------|----------------------------------------|
| 15 | Stock A (2.52 g) | Paclitaxel (17.25) | 7.5 | |
| 16 | Rape seed oil (1.1 g), PEG 400 (1.1 g), Polysorbate 60 (127 mg) | Paclitaxel (8.6) | 7.5 | |
| 17 | Ethanol (1 mL), propylene glycol (1 mL), rape seed oil (606 mg) | Budesonide (4.70) | 7.5 | |
| 18 | Castor oil (2.6 g), Polysorbate 60 (209 mg) | Budesonide (4.34) | 7.5 | |
| 19 | Stock A (2.5 g) | | | 7.5 + 83.5 mg NaCl* |

*Sodium chloride concentration in the chitosan phase is 1.1% (physiological condition is approximately 0.9%)

The compositions were stored overnight at 40° C. All the compositions solidified and formed visually homogeneous and solid "emulsions".

D. Chitosan Emulsions as Carriers of Drugs, Vitamins and Preservatives

Preparation of chitosan solution (1.0 w/w) (80 mL) Chitosan DD 49% (800 mg) was dissolved by dropwise addition of 2M HCl under constant stirring. The pH was adjusted to 6.7 and the volume adjusted to 80 mL.

Preparation of Diethyl Squarate Stock Solution in Ethanol (3,4-diethoxy-3-cyclobuten-1,2-dione) (58 mg) was dissolved in ethanol (950 µL).

Activation of chitosan solution with 3,4-diethoxy-3-cyclobuten-1,2-dione

To 30 mL of the chitosan solution described above, was added diethyl squarate stock solution (157 µL). The solution was stirred at room temperature for at least 15 minutes, to secure efficient mixing, before it was used in the preparation of the emulsions.

Preparation of Rape Seed Oil-Polysorbate Stock Solution

Polysorbate 60 (2 g) was stirred at room temperature in rape seed oil (25 g) until a homogeneously and slightly opaque solution had formed.

Preparation of Vitamin D3 Stock Solution

Vitamin D3 (5.7 mg) was dissolved in Miglyol 812 (2.97 g)

Preparation of Esomeprazole Stock Solution)

Na-Esomeprazole (43.5 mg) and 2 M HCl (1.0 equiv, 63 µL) was added to a stirred solution of Phosal 53 MCT (1.6 g) and Miglyol 812 (1.8 g). The yellow liquid phase became gradually more reddish as the omeprazole dissolved and had the colour of a dark red wine when the material was completely dissolved.

Preparation of Emulsions

Examples 20 to 22 having the composition shown in Table 4 were prepared as described hereinabove. The hydrophobic drugs/vitamins were dissolved/pre-mixed in their respective hydrophobic phases before they were added to the activated chitosan solution. In Example 22 below, methyl-4-hydroxybenzoate and propyl-4-hydroxybenzoate were dissolved in the chitosan-containing phase before addition of the hydrophobic phase.

TABLE 4

| Example | Hydrophobic phase | Emulsifier (mg) | Drug, vitamin or preservative (mg) | Activated chitosan solution (g) |
|---|---|---|---|---|
| 20 | Vitamin D3 stock solution (2.5 g) | Phosal 53 NCT (110 mg) | Vitamin D3, (4.9) | 7.5 |
| 21 | Omeprazole stock solution (2.5 g) | | Omeprazole (32) | 7.5 |
| 22 | Rape seed oil-polysorbate (2.5) | | Methyl-4-hydroxy-benzoate (15), pPropyl-4-hydroxy-benzoate (3) | 7.5 |

E. Chitosan Emulsions Prepared Using High-Pressure Homogenisation and the Subsequent Investigation of their Physical Stability Under Stressed Conditions Commercially available oils, emulsifiers and other chemicals were used without further purification. Distilled water was used in all preparations. Soybean oil and medium-chain triacylglycerol (MCT) oil were used as model oils.

The following phospholipids from Lipoid AG, Switzerland, were used as emulsifiers:

Lipoid E80 (batch 1032632-03/908)—from egg yolk, 80-85% phosphatidylcholine, 7-9% phosphatidylethanolamine Lipoid E PC S (batch 108064-03/175)—from egg yolk, 99% phosphatidylcholine, saturated Lipoid S75 (batch 776137-06/904)—from egg yolk, 71% phosphatidylcholine Lipoid S PC (batch 792036-01/948)—from egg yolk, 99% phosphatidylcholine Soybean oil was obtained from Sigma (57382; lot MKBB7610V) and MCT oil was provided by Apoteket (Miglyol 812, batch A011335). To all mixtures of emulsifier and oil were added a few drops of fat-soluble dye, Oil red O, from Sigma (00625, lot 039K1466). This aided the visualisation of any potential physical instability, particularly early tendencies to phase separation, i.e. aggregation and creaming, of the final emulsions.

A Viscosan solution was prepared by drop-wise addition of 2 M HCl (aq.) under constant stirring to chitosan (DD 44%) (31.25 g) suspended in water (2.5 L). When the chitosan had dissolved, pH was adjusted to 6.6 by the addition of 1 M NaOH (aq.) and the volume adjusted with water to give a final concentration of 1.25% (w/w) chitosan in water.

The emulsifier was added to the oil and the mixture was then heated to about 70° C. and mixed using a vortex mixer until a homogeneous dispersion was obtained. The oil mixture and the Viscosan solution were preheated on a water bath to about 60° C. The aqueous phase was added to the oil mixture under high shear mixing using an Ultra-Turrax high-shear mixer (IKA, Germany) at 9,000 rpm for about 3-4 min.

The pre-emulsion (300 mL) was homogenised at 4140 MPa (40/400 bar) using a Panda 1K high-pressure laboratory homogenizer (Niro Soavi, Italy) for 2 min (corresponding to about 2-3 cycles).

The final emulsion was then transferred to 50 mL plastic tubes (Falcon), 30 mL in each tube. Cross-linking was accomplished by the addition of 73 µL diethyl squarate (3,4-diethoxy-3-cyclobutene-1,2-dione; Acros, lot A0272633), diluted 1:10 in ethanol, and shaking for about 15 s.

The physical stability of the emulsions was investigated at stressed conditions, i.e. after storage at elevated temperature (40° C.) at several time points for up to 43 days. In some cases, this was followed by three freeze-thaw cycles, where each cycle comprised freezing at −18° C. and thawing at room temperature. Each sample was visually examined and photographed.

As references, the corresponding emulsions were prepared with pure water and without cross-linking of the chitosan solution, respectively.

The following oil-in-water emulsions (batch size 300 g) were prepared:

Example 23

| Ingredient | % (w/w) |
|---|---|
| Lipoid E80 (emulsifier) | 1.2 |
| MCT oil | 10.0 |
| Viscosan ® (1.25% chitosan in water) | ad 100.0 |

Example 24

| Ingredient | % (w/w) |
|---|---|
| Lipoid S PC (emulsifier) | 1.2 |
| Soybean oil | 10.0 |
| Viscosan ® (1.25% chitosan in water) | ad 100.0 |

Example 25

| Ingredient | % (w/w) |
|---|---|
| Lipoid E80 (emulsifier) | 1.2 |
| Soybean oil | 40.0 |
| Viscosan ® (1.25% chitosan in water) | ad 100.0 |

Example 26

| Ingredient | % (w/w) |
|---|---|
| Lipoid E PC S (emulsifier) | 1.2 |
| Soybean oil | 10.0 |
| Viscosan ® (1.25% chitosan in water) | ad 100.0 |

Example 27

| Ingredient | % (w/w) |
| --- | --- |
| Lipoid S75 (emulsifier) | 1.2 |
| Soybean oil | 10.0 |
| Viscosan ® (1.25% chitosan in water) | ad 100.0 |

Surprisingly, after 43 days of storage at 40° C., none of the emulsions showed any appreciable signs of phase separation. The corresponding emulsions prepared using pure water or Viscosan solution, i.e. a chitosan solution not subjected to cross-linking, were all less stable, resulting in severe aggregation and/or coalescence and subsequent separation into two macroscopic liquid phases, which is the expected behaviour of conventional oil-in-water emulsions stored at such harsh conditions. Two of the comparative emulsions with water were a little more stable, the comparative emulsion of Example 26, which had a small tendency to separate and the comparative emulsion of Example 27, which was stable after 43 days. However, after two freeze-thaw cycles these comparative emulsions had phase separated.

The gels of Examples 23 and 25 were mechanically processed to give fragments of an approximate size of 35 μm.

The gel of Example 23 was subjected to autoclave sterilisation at 121° C. for 21 minutes with no change in appearance or characteristics.

The invention claimed is:

1. A composition comprising:
   (i) a chitosan hydrogel comprising a chitosan component consisting of cross-linked chitosan as the sole chitosan component; and water;
   (ii) a liquid dispersed in the hydrogel; and
   (iii) an emulsifier,
   wherein the cross-linked chitosan is prepared from chitosan consisting of a randomly deacetylated linear polysaccharide consisting of 1,4-beta-linked D-glucosamine and N-acetyl-D-glucosamine residues having a degree of deacetylation of above 35 to 75%, and a bi-functional cross-linking agent, where the molar ratio of the cross-linking agent to the chitosan is 0.2:1 or less based on the number of functional groups in the bi-functional cross-linking agent and the number of deacetylated amino groups in the chitosan.

2. The composition according to claim 1 wherein the chitosan hydrogel additionally comprises a water-miscible solvent; or a water-soluble preservative, salt, buffer, drug, vitamin, cosmetic, or a mixture thereof.

3. The composition according to claim 1 wherein the liquid dispersed in the hydrogel is an oil, a pharmaceutical active agent or excipient, a cosmetic ingredient, a vitamin, a food, an agrochemical active agent or excipient, a personal care ingredient, or a mixture thereof.

4. The composition according to claim 1 wherein the dispersed liquid is present in an amount of 5 to 30% by weight based on the total weight of the composition.

5. The composition according to claim 1 comprising one or more water-insoluble active ingredients solubilised in the dispersed liquid.

6. The composition according to claim 5 wherein the water-insoluble active ingredient is a drug or vitamin.

7. The composition according to claim 1 in the form of a crushed gel.

8. A process for preparing the composition according to claim 1, the process comprising:
   providing a cross-linkable chitosan composition comprising as the sole chitosan component a chitosan consisting of a randomly deacetylated linear polysaccharide composed of 1,4-beta-linked D-glucosamine and N-acetyl-D-glucosamine residues having a degree of deacetylation of above 35 to 75% and water;
   dispersing a liquid in the cross-linkable chitosan composition; providing an emulsifier; and cross-linking the chitosan with a bi-functional cross-linking agent to form a hydrogel, wherein the molar ratio of the bi-functional cross-linking agent to chitosan is 0.2:1 or less based on the number of functional groups in the bi-functional cross-linking agent and the number of deacetylated amino groups in the chitosan.

9. The process according to claim 8 wherein the chitosan has a degree of deacetylation of 40 to 60%.

10. The process according to claim 8 wherein the chitosan, prior to cross-linking, has a molecular weight of 10 to 500 kDa.

11. The process according to claim 8 wherein the chitosan is present in the cross-linkable chitosan composition in an amount of 3% by weight or less based on the total weight of chitosan and water in the hydrogel.

12. The process according to claim 8 wherein the cross-linking is performed at acidic pH.

13. The process according to claim 8 wherein the cross-linking is performed at a pH from 6 to 10.

14. The process according to claim 8 and wherein the bi-functional cross-linking agent is added to the cross-linkable chitosan composition before the liquid is dispersed in the chitosan composition.

15. A composition made by the process of claim 8.

16. The composition according to claim 1 for use as a vaccine, a drug delivery agent, a cosmetic, a bulking agent, a thickener, a food additive, a paint additive, a paper or pulp additive or a drilling servicing fluid.

17. The composition according to claim 15 for use as a vaccine, a drug delivery agent, a cosmetic, a bulking agent, a thickener, a food additive, a paint additive, a paper or pulp additive or a drilling servicing fluid.

18. A pharmaceutical, cosmetic, food, agrochemical or personal care composition comprising the composition as defined in claim 1.

19. A pharmaceutical, cosmetic, food, agrochemical or personal care composition comprising the composition of claim 15.

* * * * *